Figure 1:
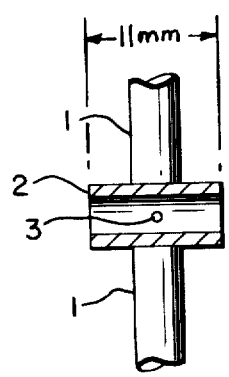

United States Patent

Woodriff

[11] 4,407,582
[45] Oct. 4, 1983

[54] METHOD AND APPARATUS FOR REDUCTION OF MATRIC INTERFERENCE IN ELECTROTHERMAL ATOMIZER FOR ATOMIC ABSORPTION SPECTROSCOPY

[75] Inventor: Ray A. Woodriff, Bozeman, Mont.

[73] Assignee: The Research and Development Institute, Inc. at Montana State University, Bozeman, Mont.

[21] Appl. No.: 224,627

[22] Filed: Jan. 12, 1981

[51] Int. Cl.³ .......................................... G01N 21/74
[52] U.S. Cl. .................................................. 356/312
[58] Field of Search ........................................ 356/312

[56] References Cited

U.S. PATENT DOCUMENTS

| 3,893,769 | 7/1975 | Woolley | 356/312 |
| 3,937,577 | 2/1976 | Dorsch | 356/312 |
| 3,979,162 | 9/1976 | George | 356/312 |
| 4,094,607 | 6/1978 | Tamm | 356/312 |

OTHER PUBLICATIONS

Lawson et al., *Spectrochimica Acta*, vol. 35 B, No. 11/12, 1980, pp. 753–763.

*Primary Examiner*—F. L. Evans
*Attorney, Agent, or Firm*—Wenderoth, Lind & Ponack

[57] ABSTRACT

The invention provides an improved method and apparatus for reduction of matrix interference in an electrothermal atomizer for atomic absorption spectroscopy. In a carbon rod atomizer within which a sample to be analyzed is atomized to the atomic state, the graphite furnace tube is electrothermally heated from the ends to the center where the sample is located. This provides sufficient thermal energy for complete decomposition of the sample molecules to the atomic state. In a first apparatus embodiment two-pronged substantially Y-shaped graphite electrode support holders for the graphite furnace tube are provided. In a second apparatus embodiment a double-walled graphite furnace tube is provided.

5 Claims, 6 Drawing Figures

U.S. Patent     Oct. 4, 1983     4,407,582

METHOD AND APPARATUS FOR REDUCTION OF MATRIC INTERFERENCE IN ELECTROTHERMAL ATOMIZER FOR ATOMIC ABSORPTION SPECTROSCOPY

BACKGROUND OF THE INVENTION

In flameless absorption spectrophotometer measurements, a sample of material which is to be analyzed is placed in a tubular graphite furnace which is electrically heated so that the sample first dries, then ashes and is eventually heated to the point at which the various elements in the sample become atomized. When the particular element or elements to be measured have been released into their atomic state, a light beam originating from a resonant line-emitting source is passed through the heated furnace tube and into a monochromator and detector, the circuitry of which determines the concentration of the desired element in the sample by measuring the intensities of appropriate portions of the resulting beam after the desired atomic element has absorbed its characteristic resonant lines.

Interferences are observed in atomic absorption spectroscopy whenever the components of the sample matrix alter the atomization time, resonance time and/or atomic population of the elements of interest relative to the atomization of the pure element in the absence of the matrix. Much study has been conducted with respect to chemical environments in which gas phase reactions prevent a species from decomposing to its constituent elements before leaving the optical path. Commercial electrothermal atomizers used in this work, e.g., Varian models CRA-63 and CRA-90 produce strongly attenuated atomic lead signals in the presence of several chloride salts. This is due to an atomizer design which heats the sample-containing atomizer center first. As a result, the analyte element often vaporizes from the furnace surface as a volatile molecule, i.e., $PbCl_2$, but encounters furnace walls which are either as hot or cooler than the surface from which it left. Therefore, insufficient thermal energy is available for complete decomposition of the molecule to atoms.

The approach to solving the problem of matrix interferences in pulse-heated electrothermal atomizers for Atomic Absorption Spectroscopy (AAS) has recently focused on proper design. Routine analysis by AAS is currently hampered by complex matrices which alter the true elemental sample populations observed by the spectrometer. Matrix-independent atomizers are therefore imperative to any laboratory that requires an increase in production and accuracy. Three main approaches to dealing with this problem are currently in practice:

(1) Chemical modification of the sample involves the use of reagents such as $H_3PO_4$ or $H_2$ gas to remove interfering chlorides during the ash cycle as HCl gas [Czobik et al. (I), *Anal. Chem.* 50, 2 (1978); Churella et al., *Anal. Chem.* 50, 309 (1978); Czobik et al. (II), *Talenta* 24, 573 (1977); Frech et al. (I), *Anal. Chim. Acta* 82, 83 (1976)], ascorbic and oxalic acids which reduce seawater interference on Co. Cu and Mn [D. J. Hydes, *Anal. Chem.* 52, 959 (1980)] and many chloride interferences on Pb by a still disputed mechanism [Hydes (supra) and McLaren et al., *Analyst* 102, 542 (1977)], excess $LiNO_3$ which binds excess Cl through formation of thermally stable LiCl [B. V. L'vov (I) *Spetrochim. Acta* 33B, 153 (1978)], and furnaces precoated with lanthanum [Thompson et al., *Analyst* 102, 310 (1977)] or molybdenum in the presence of phosphoric acid [D. J. Hodges, *Analyst* 102, 66 (1977)] to overcome various lead interferences in urine and natural waters.

(2) Selective volatilization involves the vaporization and removal of one component of the analyte-matrix system before the other is vaporized. For example, no interference is observed in the $Ni-CdCl_2$ system since the decomposition products of $CdCl_2$ leave the furnace before Ni begins to atomize. However, a severe depression of the Pb AA signal is observed for the $Pb-CdCl_2$ system since the decomposition of $CdCl_2$ to produce free Cl and the atomization of Pb occur at similar temperatures, therefore Pb and Cl vapor coexist at the same time causing formation of PbCl in the gas phase [Czobik et al. (I), supra]. The relative temporal residence of analyte and inteferent is governed primarily by their respective atomization and decomposition temperatures. However, the extent of overlap can be influenced in some cases by the atomizer length and temperature ramp of the pulse-heated atomizer. Thus, short atomizers and rapid heating will cause rapid diffusion of each species from the atomizer thereby minimizing temporal overlap. It was in this context of vapor phase interference within the atomizer that Czobik and Matousek advocated short furnace designs and short residence times despite the concurrent decrease in the analyte signal obtained [Czobik et al. (I), supra].

(3) The standard additions method assumes an equal fraction of analyte signal perturbation (depression or enhancement) by the matrix for both the analyte level originally present in the sample and added aliquots of standard solutions of the analyte. This technique is commonly used when methods (1) and (2) are unable to produce a matrix independent atomic absorption signal. Whether or not a correct result is obtained depends on the nature of both matrix and analyte.

Although the methods outlined above have provided solutions to some specific problems and in several instances produced insights into the chemistry of some analyte-matrix interaction [Johansson et al., *Anal. Chim. Acta* 94, 245 (1976); Frech et al. (II), *Anal. Chim. Acta* 82, 83 (1976)], it has become apparent that the scope of such approaches is limited. For example, multielement atomic absorption becomes impractical when performed with matrix-dependent atomizers since a single chemical pretreatment rarely works for a wide range of elements in one or a complex mixture of matrices; i.e., $H_3PO_4$ eliminates interference in the Cu-NaCl system while enhancements are observed in the Pb-NaCl system [Czobik et al. (I), supra]. Use of selective volatilization is limited in scope even for simple systems; i.e., cases where analyte and interferent appear at equal temperatures. This problem becomes even more pronounced when several elements in complex samples are to be measured simultaneously. Standard additions may not work for some elements and, unless the analyst is aware of this, erroneous results are obtained. The increased time and effort expended in determining the effectiveness and utility of the standard additions method is worth avoiding, when possible, to any laboratory handling large numbers of samples. In general, laboratory productivity is often reduced by samples with strong matrix interferences when the present matrix sensitive commercial electrothermal atomizers are utilized for routine AAS analysis. When the above "correction" procedures are applied, risk of contamination, erroneous results and analysis time are increased.

The present invention is based upon the conclusion that the best approach is to design an atomizer which produces a matrix independent atomic absorption signal. Ideally, the atoms should be designed to produce an atomization time ($\tau_1$) which is small ($\tau_2/\tau_1>1$) relative to the average residence time of an atom ($\tau_2$) in order to minimize variations in peak height and area that arise from matrix induced shifts in the appearance temperature and $\tau_1$ of the analyte. These requirements are attained with the constant temperature furnaces (CTF) of Woodriff et al. and L'vov [Woodriff et al. (I), *Spetrochim. Acta* 23B, 665 (1968) and B. V. L'vov (II), *Atomic Spectroscopy*, Israel Program for Scientific Translations, Jerusalem (1969)]. Unfortunately, in order to reduce size and simplify the design, the commercial electrothermal atomizers which have been developed subsequent to the introduction of the CTF were shortened and pulse-heated. This change in design led to the formation of matrix interferences which were not seen in the original constant temperature furnaces as Hageman et al. [Hageman et al. (I), *Anal. Chem.* 51, 1406 (1979) and Hageman et al. (II), *Appl. Spectr.* 33, 226 (1979) demonstrated. However, it was not until 1977 when L'vov proposed his platform that a change in atomizer design was considered as a means of reducing matrix interferences in pulse-heated atomizers. The fact that CTF's are free of matrix effects and that these effects can be reduced or eliminated in pulse furnaces by delaying sample introduction until the atomizer walls and internal gas are hotter than the appearance temperature of the element of interest, suggests that temperature is a key factor. Another factor is the residence time within the hot environment ($\tau_2$), which is related to length. Thus, ideally, even if analyte-molecule formation due to matrix interactions does occur, decomposition to atoms is complete before the analyte leaves the atomizer. In the case of CTF, such reactions have several seconds to reach completion since the rate of sample travel down the atomizer tube is diffusion controlled. Pulsed atomizers, however, expel the atom cloud from the atomization chamber with expanding inert gas driven by rapidly increasing wall temperature. As a consequence, residence times in most pulsed furnaces are less than 500 milliseconds. Since kinetics probably determine the relative distribution of atomic and molecular species in pulsed atomizers as suggested by Fuller [C. W. Fuller, *Analyst* 99, 739 (1974)] and supported by Holcombe [J. A. Holcombe et al., *Anal. Chem.* 51, 1205 (1979)], higher temperatures and longer tubes than required for a matrix-free CTF would be expected.

The Varian CRA-63 atomizer is the smallest (9 mm length, 3 mm i.d.) among the commercial electrothermal atomizers currently available. From the viewpoint of selective volatilization, this is advantageous. However, when this is not applicable, some of the most severe matrix interferences are seen, especially for the chlorides. Due to its small internal diameter, it is difficult to utilize a L'vov platform or some modification of it. This prompted a search for an alternate modification of the Varian design which would incorporate the simplicity and effectiveness of the L'vov platform.

BRIEF DESCRIPTION OF THE INVENTION

The present invention provides improved method and apparatus for vaporizing samples to be analyzed by atomic absorption spectroscopy. In accordance with the improved method sufficient thermal energy to vaporize the sample is provided by heating the furnace tube containing the sample to be analyzed from the ends, thereby vaporizing the sample only after the entire furnace is as hot or hotter than the center.

Two improved furnace designs are provided. In the first, two-pronged holders for the graphite sample-containing tube are provided in which electric current is allowed to pass only at the ends of the furnace tube. In the second, a double-walled furnace tube is provided which allows current to pass only across the ends of the sample-containing graphite tube.

BRIEF DESCRIPTION OF THE DRAWINGS

FIG. 1 is a top view of a prior art device;

FIG. 2 is a top view of a device of one embodiment of the present invention;

FIGS. 3A and 3B are exploded perspective views from the top and bottom respectively of the double-walled furnace embodiment of the present invention;

FIG. 4 is a sectional view assembled taken along lines 4—4 of the double-walled furnace embodiment of the invention; and FIG. 5 is a sectional view taken along line 5—5 of the double-walled furnace embodiment of the invention.

DETAILED DESCRIPTION OF THE INVENTION

There are presently available pulsed electrothermal atomizers, e.g., Varian Models CRA-63 and CRA-90. However, in such atomizers the graphite furnace tube containing the sample to be analyzed is supported by graphite electrode supports which support the furnace tube at substantially the center. This can be seen by referring to FIG. 1 which shows the graphite support electrodes 1 supporting the graphite furnace tube 2 having a sample introduction port 3. This assembly is, of course, mounted within a chamber (not shown) as is known in the art and electrical current is provided through the support electrodes from a source also not shown but also well known in the art. In such arrangement the electrical current passes through the graphite furnace tube 2 at the center thus causing the center to heat before the tube ends. This creates difficulties as previously discussed herein.

The present invention overcomes these difficulties by providing thermal energy to the ends of the furnace tube thereby heating said ends first with the center where the sample is located being heated by conduction. Large initial temperature differences between the sample-containing center of the furnace tube and the ends eliminates or decreases the interferences e.g., on Pb, normally encountered with the known atomizers of this type.

In a first embodiment the structure of the known devices is modified by providing two-pronged electrode support holders for the graphite furnace tube. Such holders are illustrated by FIG. 2 in which the electrode support holders support the graphite furnace tube 12 at the ends thereof rather than at the sample-containing center. The furnace tube also contains a sample introduction port 13.

The electrode support holders may be composed of materials which are generally known for use in producing such electrode support holders as, for example, graphite. In specific embodiments they may be machined from ⅜ inch and ⅜ inch graphite rods.

The specific configuration of the support holders 11 is not critical, the important feature residing in their being two-pronged and supporting the furnace tube at the ends thereof rather than at the center.

The furnace tube 12 may be that which is conventionally employed in such devices as for example a 9 mm tube (3 mm i.d., 5 mm o.d.) machined from Poco (Decatur, Texas) AXF-50 grade graphite. Such tubes may have a pyrolytic coating or may be used without such coating. Tubes longer than the 9 mm tube illustrated may be used and in certain instances better results can be obtained with the longer tubes. In general, 18 mm is about the practical upper limit for tubes which can be shielded by the necessary inert gas sheath from below in the currently available commercial devices.

When employing the two-pronged electrode support holder of this invention it may be necessary in view of a larger mass of the longer furnace tubes and supports to modify the power supply of the commercial devices such as the Varian CRA-63 to provide additional electrical power necessary to achieve desirable heating rates. However, those skilled in this art will readily be able to accomplish such modification.

When electrical current is passed through the two-pronged electrode supports of the present invention, the said current passes through the ends of graphite furnace tube thus first heating the ends of the said tube and permitting the sample-containing center of said tube to be heated by conduction. In this way, sufficient thermal energy is available for complete decomposition of the sample molecules to the atomic state.

The following tests illustrate this first embodiment of the present invention. In these tests, the interference of six different chlorides and one sulfate matrix on the atomic absorption signal of Pb was used.

APPARATUS AND TECHNIQUES

A. Two-Pronged Supported Atomizer.

Figure 2:
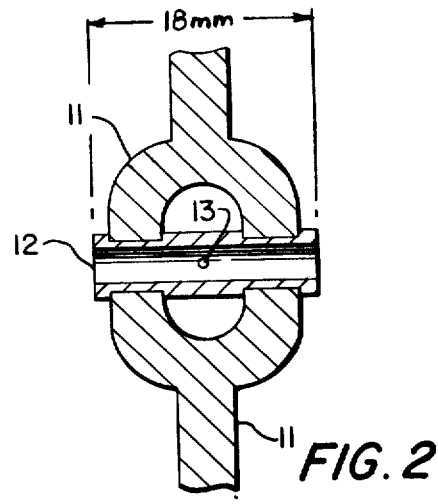

Interference studies were performed on the Varian CRA-63 atomizer with the standard pyrolytically coated 9 mm tube heated from the center using the standard supports. For comparison, an identical 9 mm tube (3 mm i.d., 5 mm o.d.) was machined from Poto (Decatur, Texas) AXF-50 grade graphite. No significant difference in recovery was noted with and without pyrolytic coating. All tubes were therefore machined from the AXF-50 graphite in the following lengths: 9 mm, 11 mm, 16 mm, and 18 mm. All tubes were 3 mm i.d. and 5 mm o.d.. Each atomizer was heated from the ends by allowing the current to flow only across the ends of the tube. This was accomplished by machining 2-pronged graphite supports from ⅜" (for 9 mm and 11 mm tubes) and ⅝" (for 16 mm and 18 mm tubes) graphite rods. FIG. 2 illustrates the ⅝" support for the 18 mm tube. 18 mm is the practical upper limit for atomizer lengths which can be shielded by the inert gas sheath from below in the Varian CRA-63 atomizer.

B. Power Supply.

A Varian CRA-63 atomizer head and power supply was used for all measurements except those made at high power levels, where a 5 KW transformer was connected in a parallel with the Varian power supply. This allowed the dry and ash steps to still be performed with the Varian supply while the atomization was initiated with a manually thrown double pole switch connected to a high voltage (208 V) variable transformer. The variable transformer controlled the voltage on the primary windings of a step-down transformer. Up to 140 amperes at 14 V could be used to heat the larger mass of the 18 mm tube with the ⅝" 2-pronged supports. This was necessary since the highest "atomize" setting on the CRA-63 power supply was insufficient to provide heating rates comparable to the 9 mm and 11 mm tubes operated at an atomize setting of 8.5. Significant improvements were obtained with the higher power levels.

C. Optics and Electronics.

A Westinghouse PB hollow-cathode lamp operated at 6 ma was the light source. A dual channel monochromator constructed in this laboratory [Woodriff et al. (II), *Appln. Spectr.* 27, 181 (1973)] was operated at the 283.3 nm lead resonance line and a bandpass of 0.45 nm for all measurements. The 283.3 nm lead line was chosen because the background absorbance there is lower than at 217.0 nm.

The detector was a IP128 photomultiplier operated at 890 V. The PMT signal was fed into an Ithaco (Ithaco, NY) lock-in amplifier with a time constant set at 10 ms. This output was connected in parallel to an Omniscribe (Austin, Texas) strip chart recorded (for peak height measurement) a logarithmic amplifier followed by a V-F converter and counter (for peak area recording) and a Tektronic 564 dual trace stage oscilloscope (to record peak shapes and positions and measure $\tau_1$ and $\tau_2$). The oscilloscope trace was triggered by the voltage level produced at the onset of the atomization stage. No background corrector was used. This allowed separate measurement of the background signal and comparison of its magnitude among the various atomizer designs studied.

D. Temperature Measurements.

The temperature of the outside surface of the atomizer was monitored with a phototransistor. The transistor output was fed to the inverting input of a 741 operational amplifier with a diode in feedback. This output was then recorded simultaneously with the absorption curves of the oscilloscope. In order to obtain separate recordings for the temperature ramps generated at the center and ends of the atomizers, the phototransistor was placed in a blackened metal tube and light from a region 3 mm in diameter was focused on the transistor base through a lens. It was also necessary to use a graphite baffle placed over the top of the atomizer head when temperature measurements at the center were recorded. This prevented light from the hotter tube ends from reaching the phototransistor. A measurable temperature difference between the center and ends of an atomizer was discernable only for 16 mm and 18 mm tubes. Temperature ramps given for 9 mm and 11 mm tubes are for the entire atomizer.

E. Reagents and Operating Conditions.

Simple matrix solutions were prepared from analytical reagent grade interferent salts and deionized water. A 1000 µg/ml lead reference standard was prepared by dissolving the metal in distilled reagent grade nitric acid. A 200 ppb lead solution was used in the interference studies shown in Tables I and II. 2.4 µl Aliquots, delivered from a Unimetrics variable micropipet, were used for all solutions. The micropipet was calibrated and found to consistently deliver 2.4 ± 0.1µ of solution.

Solutions analyzed in the 9 mm and 11 mm atomizers were dried at a setting of 3.0 (dry stage) for 25 seconds and ashed at a setting of 6.0 (ash stage) for 15 seconds.

Although ashing was not necessary for the synthetic solutions used, an ash step was carried out to simulate conditions often used in an ET AA analysis. Atomization was run at a setting of 8.5 for 3 seconds which corresponded to a temperature ramp of 1.5° K./ms. Line power to the CRA-63 supply was 115 V.

Due to their higher mass, 16 mm and 18 mm atomizers were dried at a setting of 3.5 for 30 seconds and ashed at a setting of 6.5 for 15 seconds. Atomization using the CRA-63 power supply was carried out at a setting of 10 which corresponded to a temperature ramp of 0.23 °K./ms at both the center and ends of the tube. Atomization using the 5.0 KW transformer produced temperature ramps of 0.1 °K./ms at the center and 1.9 °K./ms at the ends using approximately 120 amperes. Higher power was tested but temperature ramps were not recorded. A flow of 10 l/min of nitrogen was used to shield the graphite parts in all measurements.

RESULTS AND DISCUSSION

Tables I and II list the percent recovery for a fixed amount of Pb in six chloride and one sulfate matrices. Greater recoveries were often obtained by using peak areas rather than peak heights. The largest differences (up to 20%) resulted when NaCl, FeCl$_3$, CuCl$_2$ or CaCl$_2$ were the added interferent. Observation of peak shapes on the storage oscilloscope revealed peak broadening, double peaks, and decreases in $\tau_1$ as the cause. Iron (III) chloride produced a broadened peak while CuCl$_2$ and CaCl$_2$ gave double peaks. The double peaks persisted in all cases for CuCl$_2$; however, only a single peak was observed for CaCl$_2$ in longer (16 mm and 18 mm) end-heated atomizers. Similarly, a sharp peak with a reduced $\tau_1$ (which produces an increased peak height) observed for NaCl in the 9 mm CRA-63 atomizer became a slower rising peak identical to pure lead nitrate in the 16 mm and 18 mm end heated atomizers.

Studies of $\tau_1$, $\tau_2$ and appearance temperatures must be interpreted with caution since many factors are operating simultaneously. For example, the atomization time, $\tau_1$, is shorter for Pb in the presence of any of the matrices studied than pure Pb(NO$_3$) when atomization occurs in the standard CRA-63 9 mm atomizer (e.g., Pb with ZnSO$_4$; $\tau_1 = 270$ ms Pb; $\tau_1 = 470$ ms heating rate of 1.5 °K./ms). In contrast, when atomizing in the 18 mm end-heated tube (1.1 °K./ms at center) $\tau_1$ is nearly equal for Pb with and without an interferent matrix present (e.g., Pb with ZnSO$_4$; $\tau_1 = 490$ ms Pb; $\tau_1 = 480$ ms). Since the measured heating rate is slightly lower for the 18 mm atomizer, a comparison was made to the lower heating rate (0.23 °K./ms) of the same tube powered by the CRA-63 supply: Pb with ZnSO$_4$; $\tau_1 = 450$ ms Pb; $\tau_1 = 480$ ms.

The agreement between the $\tau_1$ values obtained in the 18 mm end-heated atomizer at two different heating rates suggests that the small changes in heating rates used are not the source of the atomization time changes. Since $\tau_1$ is constant for an element with a given set of atomization parameters (i.e., atomizer surface, heating rate and chemical environment) independent of the amount atomized [Stugeon et al., *Anal. Chem.* 47, 1250 (1975) and Smeyers-Verbeke et al., *Anal. Chem.* 50, 10 (1978)], the changes observed seem to reflect a change in the chemistry of atomization. The consistent $\tau_1$ values for lead nitrate in all three cases indicated that heating the ends of an atomizer first affects the analyte-matrix chemistry. The details of this change are unknown and beyond the scope of the present application; however, temperature is the key ingredient. It may be related to the higher gas temperature above the sample. The expanding hot gas at the atomizer ends might rapidly heat the gas throughout the tube. How this would alter the atomization rate of the volatile lead chloride formed in the presence of chloride matrices is uncertain.

In addition to maintaining a greater temperature difference between the atomizer center and ends, longer atomizers also provide increased sensitivity. Table III shows the increase in peak height as atomizer length increases. Peak area, however, did not increase significantly for comparable heating rates in changing from a 9 mm to an 18 mm atomizer. This may be due to the higher heating rate at the atomizer end which causes a more rapid expansion of the gas within the furnace than would be expected from center heating rate alone.

Peak area and residence time increased for the 18 mm atomizer heated at 0.23 °K./ms. For the 9 mm atomizers, $\tau_2 = 200$ ms which increased to 280 ms for the 18 mm tubes at lower heating rates. Upon increasing the heating rate, however, it decreased to 200 ms.

TABLE I

Percent Recovery Obtained for 480pg Pb in 3 Chloride Matrices.[a]

|  | 24 µg NaCl | 2.4 µg MgCl$_2$ | 0.48 µg MgCl$_2$ | 2.4 µg ZnCl$_2$ | 0.48 µg ZnCl$_2$ |
|---|---|---|---|---|---|
| 9mm[b] center | 68 ± 6 | 0 | 5 | 47 ± 6 | 68 ± 5 |
| 9mm[b] end | 69 ± 6 | 0 | 5 | 49 ± 6 | 82 ± 9 |
| 11mm[b] end | 78 ± 7 | 4 | 12 | 56 ± 7 | 86 ± 8 |
| 16mm[c] end | 92 ± 6 | 46 ± 6 | 73 ± 6 | 75 ± 6 | 87 ± 6 |
| 18mm[c] end | 100 ± 5 | 48 ± 6 | 88 ± 7 | 82 ± 6 | 92 ± 6 |
| 18mm[d] end | 102 ± 5 | 87 ± 6 | 100 ± 5 | 90 ± 5 | 103 ± 6 |

[a]Peak area measurements.
[b]Heating rate of 1.5° K/ms. 'Center' refers to current passed across center of atomizer by commercial CRA-63 supports. 'End' refers to current passed across ends of atomizer by 2-pronged supports.
[c]Heating rate of 0.23° K/ms at atomizer center.
[d]Heating rate of 1.1° K/ms at atomizer center.

TABLE II

Percent Recovery Obtained for 480pg Pb in 4 Different Matrices.[a]

|  | 1.41 µg FeCl$_3$ | 2.4 µg CuCl$_2$ | 0.48 µg CaCl$_2$ | 2.4 µg CaCl$_2$ | 0.48 µg CaCl$_2$ | 2.4 µg ZnSO$_4$ |
|---|---|---|---|---|---|---|
| 9mm[b] center | 0 | 2 | 17 ± 5 | 10 ± 8 | 69 ± 9 | 27 ± 8 |
| 9mm[b] end | 0 | 2 | 18 ± 5 | 20 ± 5 | 68 ± 8 | 80 ± 8 |
| 11mm[b] end | 0 | 2 | 18 ± 5 | 56 ± 7 | 74 ± 8 | 75 ± 8 |
| 16mm[c] end | 33 ± 8 | 35 ± 8 | 65 ± 6 | 65 ± 6 | 80 ± 6 | 73 ± 8 |
| 18mm[c] end | 45 ± 9 | 42 ± 8 | 100 ± 5 | 75 ± 6 | 88 ± 6 | 71 ± 9 |
| 18mm[d] end | 70 ± 8 | 67 ± 8 | 98 ± 5 | 113 ± 4 | 100 ± 4 | 90 ± 7 |

[a]Peak area measurements.
[b]Heating rate of 1.5° K/ms. 'Center' refers to current passed across center of atomizer by commercial CRA-63 supports. 'End' refers to current passed across ends of atomizer by 2-pronged supports.
[c]Heating rate of 0.23° K/ms at atomizer center.
[d]Heating rate of 1.1° K/ms at atomizer center.

TABLE III

| Effect of Increasing the Amount of Pb Constant Interferent Level.[a] | | | | | |
|---|---|---|---|---|---|
| Pb (ng) | Ratio[b] MgCl$_2$/Pb | Recovery (%) | Pg (ng) | Ratio[c] MgCl$_2$/Pb | Recovery (%) |
| 0.24 | 2000 | 58 ± 5 | .24 | 10,000 | 38 ± 5 |
| 0.48 | 1000 | 74 ± 5 | .48 | 5,000 | 46 ± 5 |
| 0.96 | 500 | 83 ± 4 | .72 | 3,333 | 55 ± 6 |
| 1.44 | 333 | 92 ± 5 | .96 | 2,500 | 55 ± 6 |

[a]16mm atomizer end heated; heating rate at center 1.1° K/ms.
[b]0.48 μg MgCl$_2$
[c]2.4 μg MgCl$_2$ These tests demonstrate that by heating a pulsed electrothermal atomizer at the ends and allowing the center to heat by conduction, enough thermal energy can be imparted to the vaporized sample for effective decomposition of the analyte-matrix vapor phase molecules.

In a second embodiment of this invention there is provided a double-walled furnace tube which allows electrical current to pass only across the ends of the tube thus causing the ends to be heated first while the sample-containing center portion of the tube is heated by conduction and radiation.

In connection with the first described embodiment herein, it has been noted that the larger mass as compared with the commercially employed atomizer apparatus in some cases requires modification of the power supply to provide adequate power for heating. Also modification is required of the commercial equipment to replace the supplied electrode support holders with the instantly disclosed two-pronged support holders. Also in the case of low volatility elements, temperatures sufficient to completely atomize the sample may in some cases not be attained with the two-pronged support. The double-walled furnace tube provided as the second embodiment herein overcomes those disadvantages. The standard straight electrode support holders provided in the commercial equipment, e.g., the Varian CRA-63, can be employed with the double-walled tube. Since the mass of the system using the double-walled furnace tube more closely approximates that of the commercial system, the standard power supply provided in the commercial device may be employed. Also since the entire outer sleeve of the double-walled furnace tube (as described hereinafter) heats up uniformly, the furnace tube center portion heats directly by radiation from the sleeve. The entire furnace tube thus attains a spatial constant temperature fairly quickly (~0.5 sec.) and therefore can be used to analyze low volatility elements as well as the commercially available units while retaining the advantages of end-heating.

In employing the double-walled furnace tube care must be taken in installing it between the electrode support holders. Due to the fragile nature of the outer sleeve, care must be taken not to crack the outer sleeve. Also care must be taken not to permit the support holders to bend the outer sleeve inward since this may permit arcing between the sleeve and the inner core tube at the center. This would allow the center to heat first thereby lowering recovery rates for the samples.

This embodiment will be described with reference to the drawings.

Figure 3A:
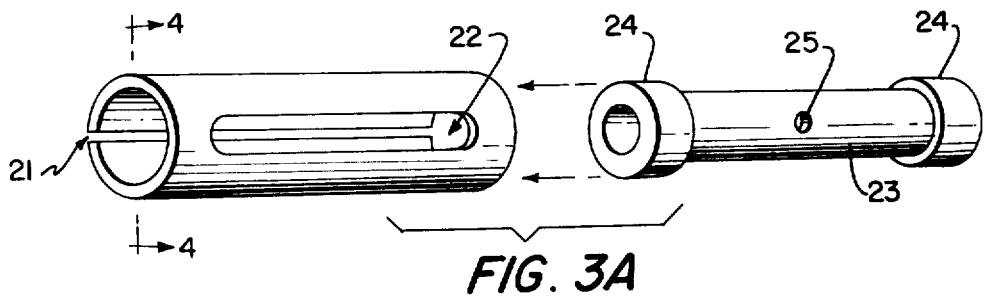
Figure 3B:
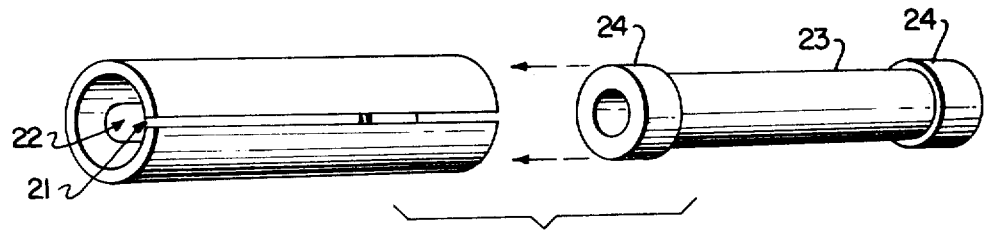
Figure 4:
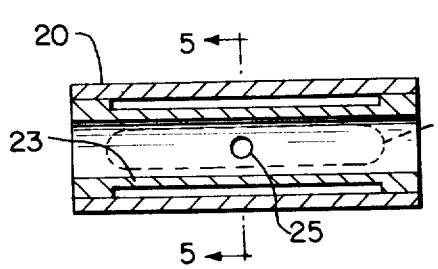
Figure 5:
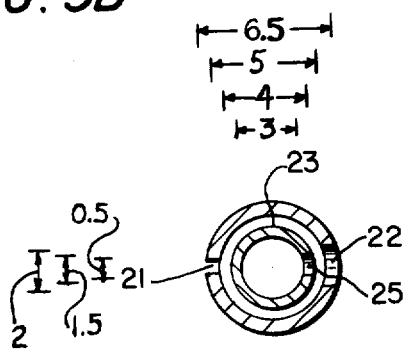

Referring to FIGS. 3A and 3B which represent perspective views from the top and bottom respectively, a graphite sleeve 20 of an open-ended cylindrical shape is provided. The sleeve contains a slit 21 which extends the full length of the sleeve and which is parallel to the axis. Additionally, the sleeve contains an elongated aperture 22 which is substantially diametrically opposite the slit and the elongation of which is substantially parallel with the slit.

Also provided is a graphite core 23 having a hollow cylindrical body portion and having shoulders 24 around the opposite ends. The outside diameter of the shoulders is such that the core will slide into and frictionally engage with the sleeve. The core contains a sample introduction port at substantially the axial center, which port aligns with the elongated aperture of the sleeve when the sleeve and core are frictionally engaged. This port extends through only one cylindrical wall to permit introduction of a sample which is to be analyzed.

When the core and sleeve are engaged it will be seen that the shoulders of the core are in contact with the inner surface of the sleeve but the body portion of the core is separated therefrom by a distance equal to the height of the shoulders. This distance must be sufficient to prevent electrical arcing between the sleeve and the center portion of the core. In this respect it is noted that the furnace tube will be mounted in a carbon rod atomizer with electrode support holders contacting the outer surface of the sleeve at substantially the axial center and at the sides thereof. Electrical current will pass from an electrode into the sleeve at the center. Due to the slit and elongated aperture in the sleeve and due to the space between the sleeve and the body portion of the core, it must pass to the ends of the sleeve and the shoulders of the core and then to the remaining electrode. The sleeve and core are thus heated from the ends to the center thereby achieving the advantages of the invention. By doing so the atomization of the sample which is located at the center of the tube is delayed until the remainder of the chamber is sufficiently hot to dissociate gaseous compounds formed between analyte atoms and atoms of the interfering matrix such as Cl, Br, I, F or S.

The dimensions which are provided on the drawings are provided to illustrate the invention and may, of course, be varied without departing from the concept of the invention.

Experiments were conducted using the double-walled furnace tube as described above. Table IV sets forth the recovery data for lead in several chloride and one sulfate matrix. The commercial Varian CRA-63 was employed using the double-walled furnace tube of the present invention.

TABLE IV

| | PERCENT RECOVERIES FOR Pb OBTAINED USING A DOUBLE-WALLED GRAPHITE FURNACE | | | | | | | | | | |
|---|---|---|---|---|---|---|---|---|---|---|---|
| | 10,000 ppm NaCl | 1,000 ppm MgCl$_2$ | 200 ppm MgCl$_2$ | 1,000 ppm ZnCl$_2$ | 200 ppm ZnCl$_2$ | 586 ppm FeCl$_3$ | 1,000 ppm CuCl$_2$ | 200 ppm CuCl$_2$ | 1,000 ppm CaCl$_2$ | 200 ppm CaCl$_2$ | 1,000 ppm ZnSo$_4$ |
| CRA-63[a] (9mm) | 68 | 0 | 5 | 47 | 68 | 0 | 2 | 17 | 10 | 69 | 27 |
| 11mm | 62 | 12 | 78 | 54 | 88 | 14 | 2 | 75 | 77 | 78 | 66 |

TABLE IV-continued

PERCENT RECOVERIES FOR Pb OBTAINED USING A DOUBLE-WALLED GRAPHITE FURNACE

| | 10,000 ppm NaCl | 1,000 ppm $MgCl_2$ | 200 ppm $MgCl_2$ | 1,000 ppm $ZnCl_2$ | 200 ppm $ZnCl_2$ | 586 ppm $FeCl_3$ | 1,000 ppm $CuCl_2$ | 200 ppm $CuCl_2$ | 1,000 ppm $CaCl_2$ | 200 ppm $CaCl_2$ | 1,000 ppm $ZnSo_4$ |
|---|---|---|---|---|---|---|---|---|---|---|---|
| 18mm | 94 | 76 | 100 | 80 | 98 | 94 | 78 | 100 | 99 | 100 | 67 |

[a]Standard Varian CRA-63 single wall tube used for comparison.

What is claimed is:

1. In a method for sample analysis by atomic absorption spectroscopy wherein a chemical sample is atomized by pulsed electrothermal energy from a carbon rod atomizer containing graphite electrode support holders and a graphite furnace tube, the improvement according to which the ends of the sample-containing furnace tube are heated first by passing electrical current only through said ends followed by heating the center of the furnace tube by conduction thereby providing sufficient thermal energy for complete decomposition of the sample molecules to the atomic state.

2. A method according to claim 1 wherein the end first heating is achieved by employing two-pronged, substantially Y-shaped graphite electrode support holders so that electrical current supplied through said electrode support holders passes through the ends of said graphite furnace tube rather than the center thereof.

3. A method according to claim 1 wherein the end first heating is achieved by employing a graphite furnace tube which comprises an open-ended cylindrical graphite sleeve having (a) a slit therein which is parallel to the axis and which extends the full length of the sleeve, and (b) having an elongated aperture therein which is substantially diametrically opposite said slit the elongation of said aperture being substantially parallel with said slit, and a graphite core having a hollow cylindrical body portion and having shoulders around the opposite ends, the outside diameter of the shoulders being such that they will frictionally engage within the inside diameter of the said sleeve, said core having a sample introduction port at substantially the axial center thereof which port aligns with the said elongated aperture when the sleeve and core are frictionally engaged, the axial length of the core being substantially the same as the axial lengths of the sleeve.

4. In a carbon rod atomizer for atomizing a chemical sample for analysis by atomic absorption spectroscopy said atomizer comprising graphite electrode support holders and an open-ended graphite furnace tube into which the sample to be analyzed is introduced, said furnace tube being supported by and having pulsed electrical energy supplied by said support holders, the improvement according to which the graphite electrode support holders are two-pronged, substantially Y-shaped so that electrical current supplied through said electrode support holders passes through the ends of said graphite furnace tube rather than the center thereof.

5. A graphite furnace tube for employment in a carbon rod atomizer which comprises an open-ended cylindrical graphite sleeve having (a) a slit therein which is parallel to the axis and which extends the full length of the sleeve, and (b) having an elongated aperture therein which is substantially diametrically opposite said slit the elongation of said aperture being substantially parallel with said slit, and a graphite core having a hollow cylindrical body portion and having shoulders around the opposite ends, the outside diameter of the shoulders being such that they will frictionally engage within the inside diameter of the said sleeve, said core having a sample introduction port at substantially the axial center thereof which port aligns with the said elongated aperture when the sleeve and core are frictionally engaged, the axial length of the core being substantially the same as the axial lengths of the sleeve.

* * * * *